United States Patent [19]

Clark et al.

[11] B 3,995,444
[45] Dec. 7, 1976

[54] ORGAN PERFUSION SYSTEM

[75] Inventors: Robert A. Clark, Garden Grove; John P. Hall, Irvine, both of Calif.

[73] Assignee: American Hospital Supply Corporation, Evanston, Ill.

[22] Filed: Nov. 8, 1974

[21] Appl. No.: 522,009

[44] Published under the second Trial Voluntary Protest Program on February 17, 1976 as document No. B 522,009.

[52] U.S. Cl. .................. 62/306; 62/376; 128/1 R; 128/DIG. 3; 195/1.7; 195/127
[51] Int. Cl.² .......................................... B01F 3/04
[58] Field of Search ........... 195/1.7, 127; 128/1 R, 128/DIG. 3; 62/64, 306, 376

[56] References Cited
UNITED STATES PATENTS

| | | | |
|---|---|---|---|
| 3,406,531 | 10/1968 | Swenson et al. | 62/306 |
| 3,545,221 | 12/1970 | Swenson et al. | 62/306 |
| 3,729,948 | 5/1973 | Schwartz | 62/64 |
| 3,777,507 | 12/1973 | Burton et al. | 62/306 |
| 3,810,367 | 5/1974 | Peterson | 62/457 |

*Primary Examiner*—William F. O'Dea
*Assistant Examiner*—Ronald C. Capossela
*Attorney, Agent, or Firm*—Tilton, Fallon, Lungmus, Chestnut & Hill

[57] ABSTRACT

A system for extracorporeal perfusion of human organs wherein a pulsatile flow of cold perfusate is circulated through an organ intended for transplantation. The system includes a perfusion chamber, a heat exchanger comprising an ice water bath containing a coil of tubing through which perfusate is circulated, and a pulsatile pump interposed in the line between the heat exchanger and the perfusion chamber, downstream of that exchanger, for drawing cold perfusate through the exchanger and directing it in a series of regular pulses to the organ. The system is particularly adapted for use in a compact portable perfusion unit.

7 Claims, 1 Drawing Figure

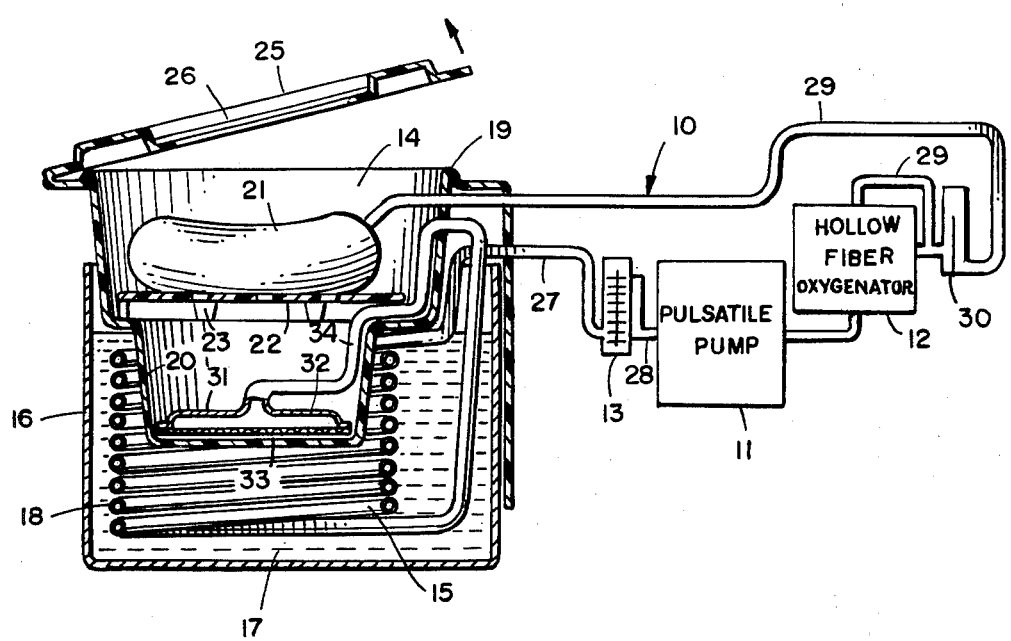

ORGAN PERFUSION SYSTEM

BACKGROUND

Belzer et al U.S. Pat. Nos. 3,632,473 and 3,753,865 disclose a widely-accepted system for preserving organs such as kidneys for transplantation. Perfusate (plasma) is pumped in a series of regular pulses through a heat exchanger where it is cooled to a temperature of about 4° to 8° C. and is then delivered to an organ supported in a perfusion chamber. Since it is necessary for effective organ preservation that the perfusate be delivered to the organ in a series of regular pulses, such an exchanger must be of the type which will not appreciably dampen the pulsatile flow. Consequently, such an arrangement does not permit the use of an exchanger having an extended tubular heat-conductive coil into which the perfusate is pumped because any substantial length of tubing would have the effect of destroying the pulse wave.

Portable perfusion units have recently been developed in which pulsatile flow is maintained through the heat exchanger by pumping the perfusate into a compartment which is closed, except for an inlet (communicating with the pump) and an outlet (communicating with the organ in the perfusion chamber), so as to avoid damping out the pulses. Cooling is achieved by circulating cold water through a tubular coil disposed within the compartment. Such a system requires two pumps, one for the perfusate and the other for the water, an obvious disadvantage in terms of bulk, weight, and complexity, especially in a portable unit. Further, to achieve sufficient dwell time to cool the perfusate, the compartment must be of substantial size and the perfusate flow rate must be relatively low. Even so, appreciable differences may develop between the temperature of the water and the lowest temperature reached by the perfusate. For example, where ambient temperatures are relatively high, a temperature differential of 5° or more may exist between the temperature of the ice water and that of the perfusate as it passes from the exchanger.

SUMMARY

It is therefore an object of this invention to provide a system which overcomes the aforementioned disadvantages and defects of prior organ perfusion systems. Specifically, it is an object to provide a compact, reliable, single-pump perfusion system or apparatus in which perfusate is quickly cooled to a predetermined temperature by circulating it through a coil of heat-conductive tubing immersed in a coolant bath, and is then delivered in regular pulses to an organ supported within a perfusion chamber.

An important aspect of this invention lies in recognizing that perfusate may be effectively pumped through the coil of a heat exchanger by locating the pump on the downstream side of that exchanger. Perfusate is thereby drawn rather than driven through the exchanger and, since the pump is on the exchanger's downstream side, an extended length of heat-conductive tubing may be used to achieve rapid cooling of the perfusate without at the same time destroying the pulse wave of the fluid to be delivered to the organ. The coil is supported in a substantially constant-temperature ice bath, thereby eliminating the need for a second pump for circulating coolant. Tubing lengths of 20 feet or more may be coiled in the exchanger to provide highly effective cooling of the perfusate while at the same time maintaining relatively rapid flow through the exchanger. Because of the substantial time required for the perfusate to pass through the coil, a close matching of bath and perfusate temperatures may be achieved despite a wide variation in ambient temperatures.

The system also includes an oxygenator in the flow circuit between the pulsatile pump and the organ supported within the perfusion chamber. It has been found that by using a conventional hollow fiber oxygenator and circulating the perfusate through the multiplicity of hollow fibers thereof, effective oxygenation of the perfusate may be achieved without damping out the pulse wave. If desired, a flowmeter may be located in the line between the heat exchanger and the pump for measuring the rate of flow of perfusate through the apparatus.

Other advantages and objects of the invention will become apparent as the specification proceeds.

DRAWING

The drawing is a partially diagrammatic view of an organ preservation system embodying the present invention, the heat exchanger and perfusion chamber of the system being shown in vertical section.

DESCRIPTION

In the drawing, the numeral 10 generally designates a system or apparatus comprising a pulsatile pump 11, an oxygenator 12, a flowmeter 13, a perfusion chamber 14, and a heat exchanger 15. The heat exchanger includes an open-topped container 16 suitable for retaining a quantity of ice water 17. Within container 16 is a cooling coil 18 of tubular plastic material. While other materials might be used, a plastic such as low density polyethylene has been found particularly effective because of its durability, resilience, low cost, ease of sterilization, and adequate thermal conductivity.

The perfusion chamber 14 constitutes the upper compartment of a casing 19, the lower compartment or well portion 20 of that casing being received in ice water bath 17 and being surrounded by at least the upper portion of or uppermost loops of the vertically oriented coil 18. The upper and lower compartments 14 and 20 are in direct communication with each other so that perfusate draining from a kidney or other organ 21 will collect in the well defined by the lower compartment. The organ may be supported on a perforated platform or panel 22 which, in the illustration given, is provided with legs 23 resting upon a shoulder 24 extending about the rim of the well. A cover 25, which may include a transparent panel 26, is shown as hingedly joined to casing 19 for closing the top opening of the perfusion chamber and for protecting the organ supported therein. In a preferred embodiment of the invention, the entire casing 19 is formed of a suitable inexpensive plastic material such as polypropylene. To reduce risks of contamination, the casing 19, coil 18, and all other illustrated components of the system except pump 11 and container 16, may be made sufficiently inexpensive to permit disposal after a single use. It will become more apparent as the specification proceeds that all of such disposable components are connected in circuit with each other and thus may be regarded as an integrated replaceable assembly or cassette for the organ perfusion system.

The flow circuit comprises conduit segments 27, 28 and 29 extending from the heat exchanger coil 18 to flowmeter 13, then from the flowmeter past or through pulsatile pump 11 to oxygenator 12, and finally from the oxygenator to the cannulated organ 21 supported within the perfusion chamber 14. A bubble trap 30 is interposed in the line between the oxygenator and the perfusion chamber to prevent gas bubbles from entering the organ through conduit 29. The bubble trap 30, flowmeter 13 and hollow fiber oxygenator may all be of conventional construction and, since such components are well known in the art, a detailed showing and description are believed unnecessary herein. Pulsatile pump 11 may be of the type disclosed in U.S. Pat. Nos. 3,632,473 and 3,753,865 although other pumps of similar design may be used.

Within the lower compartment or well of casing 19 is a filter assembly 31. The assembly consists essentially of an inverted cup-shaped intake member 32 having a filter membrane 33 extending across the mouth thereof. Conduit segment 34 extends from the filter assembly to the inlet of coil 18. Consequently, perfusate flowing from organ 21 drains downwardly into well 20 where it is then filtered before passing into heat exchanger coil 18.

As pulsatile pump operates, cold perfusate is drawn from the discharge end of the cooling coil through conduit segments 27 and 28. Since coil 18 is of substantial length and is totally immersed in ice water bath 17, the perfusate is quickly cooled to substantially the same temperature as the bath itself regardless of a wide range of ambient temperatures. In one embodiment of the invention, a coil consisting of approximately 22 feet of polyethylene tubing has been used in a system capable of lowering the temperature of perfusate from room temperature to approximately 4° to 8° C. (as delivered to the organ) in 10 minutes or less. Such rapid cooling is achieved without a plurality of pumps and without destroying the pulse wave of the delivered perfusate because of the relationship of parts and, in particular, because of the location of pump 11 downstream of heat exchanger 15.

While in the foregoing we have disclosed an embodiment of the invention in considerable detail for purposes of illustration, it is to be understood by those skilled in the art that many of those details may be varied without departing from the spirit and scope of the invention.

We claim:

1. An organ perfusion system comprising a chamber adapted to support an organ requiring perfusion, a pulsatile pump, a heat exchanger, and conduit means connecting the chamber, pump, and exchanger for the circulation of cold perfusate through an organ supported within the chamber, wherein the improvement comprises
said heat exchanger including a container for holding ice water and a cooling coil of tubular thermally-conductive material therein, said coil being connected in circuit with said pump and perfusion chamber for cooling perfusate circulated therethrough, said pulsatile pump being disposed downstream of said heat exchanger and upstream of said perfusion chamber for drawing cold perfusate from said coil and pumping the same in a series of regular pulses to an organ supported within said chamber.

2. The system of claim 1 in which a flowmeter is interposed in said circuit between said coil and pump for indicating the rate of flow of perfusate passing through said circuit.

3. The system of claim 1 in which a hollow fiber oxygenator is interposed between said pump and said perfusion chamber in said circuit.

4. The system of claim 1 in which a casing is provided with communicating upper and lower compartments, said upper compartment defining said perfusion chamber and said lower compartment being disposed within the portion of said container adapted to hold said ice water bath and said cooling coil.

5. An organ perfusion system comprising a chamber adapted to support an organ requiring perfusion, a pulsatile pump, a heat exchanger, and conduit means connecting the chamber, pump, and exchanger for the cirulation of cold perfusate through an organ supported within the chamber, wherein the improvement comprises
said heat exchanger including a container for holding ice water and a cooling coil of tubular thermally-conductive material therein, said coil being connected in circuit with said pump and perfusion chamber for cooling perfusate circulated therethrough, said pulsatile pump being disposed downstream of said heat exchanger and upstream of said perfusion chamber for drawing cold perfusate from said coil and pumping the same in a series of regular pulses to an organ supported within said chamber, said casing being provided with communicating upper and lower compartments, said upper compartment defining said perfusion chamber and said lower compartment being disposed within the portion of said container adapted to hold said ice water bath, said coil being oriented with its axis extending vertically and at least some of the loops thereof extending about said lower compartment of said casing.

6. The system of claim 5 in which said coil is oriented with its axis extending vertically, said lower compartment being surrounded by said coil.

7. The system of claim 5 in which a portion of said conduit means extends between said lower compartment and said coil, and fluid-filtering inlet means disposed within said lower compartment and communicating with said portion of said conduit means for filtering perfusate drawn into said coil upon operation of said pump.

* * * * *